United States Patent [19]

Woodford et al.

[11] Patent Number: 4,690,154

[45] Date of Patent: Sep. 1, 1987

[54] VENTED SYRINGE

[76] Inventors: Timothy Woodford; John Cheraso, both of 795 Northlake Blvd., North Palm Beach, Fla. 33408

[21] Appl. No.: 740,514

[22] Filed: Jun. 3, 1985

[51] Int. Cl.⁴ ............................................. A61B 5/14
[52] U.S. Cl. .................................... 128/765; 128/766; 604/231; 604/236
[58] Field of Search ............... 128/760, 761–766, 128/771; 604/122, 229, 231, 236

[56] References Cited

U.S. PATENT DOCUMENTS

| | | | |
|---|---|---|---|
| 3,577,980 | 5/1971 | Cohen | 128/766 X |
| 3,776,218 | 12/1973 | Svensson | 128/765 |
| 4,257,426 | 3/1981 | Bailey | 128/765 X |
| 4,266,557 | 5/1981 | Merry | 128/763 |
| 4,299,238 | 11/1981 | Baidwan et al. | 604/122 X |
| 4,372,325 | 2/1983 | Raitto | 128/763 |
| 4,424,817 | 1/1984 | Williams | 128/766 |
| 4,466,446 | 8/1984 | Baidwan et al. | 604/236 X |

Primary Examiner—William E. Kamm
Assistant Examiner—Angela D. Sykes
Attorney, Agent, or Firm—Malin, Haley & McHale

[57] ABSTRACT

A vented blood gas syringe is capable of allowing arterial blood to enter into a specimen chamber due to blood pressure or due to the aspirating the blood into the chamber where insufficient blood pressure of the patient exists. The blood gas syringe is fabricated of conventional parts modified for venting. The plunger of a conventional syringe has air passages through the lower rib thereof to allow air to pass into the air space formed by the body of the plunger. The passages are further sized to restrict the flow of blood therethrough. A slice is made in the upper rib and at least one air passage is provided from the air space between the ribs to the slice. The upper portion of the upper rib above the slice becomes a flap which can act as a valve resting on a seat formed by the slice to allow air to pass upward but not downward.

13 Claims, 6 Drawing Figures

VENTED SYRINGE

BACKGROUND OF THE INVENTION

This invention relates to a vented syringe and more particularly to such a syringe useful in obtaining a specimen of blood from an artery for use in blood gas analysis.

For many years the medical profession has used the blood gas test as a useful tool in making diagnostic determinations, particularly with respect to a patient's respiratory or metabolic functions. The blood upon which a blood gas test is performed is normally obtained from the artery of the patient. typically, this is done with a special type syringe which can be preset to a desired amount such as 2 or 3 cubic centimeters. The needle attached to the syringe is inserted into the artery and, normally, blood pressure forces the blood into the preset specimen chamber portion of the syringe. In order to allow the blood to flow into the syringe the piston portion of the syringe must be vented to allow the air displaced by the entering blood to escape. For example, see U.S. Pat. No. 3,674,181 to Marks et al, U.S. Pat. No. 4,299,238 to Baldwan et al. and U.S. Pat. No. 4,361,155 to Anastasio.

By venting the plunger to allow the air to escape as the blood enters the specimen chamber, a path also exists for blood to escape from the chamber and to spill into the surrounding area outside the specimen chamber. The blood spill is not only messy, but also is unhealthy to the technician drawing the blood. One attempt to solve this problem in the past has been the insertion of a membrane designed to pass air, but not liquid (e.g. blood) into the air passage. For example, see U.S. Pat. No. 4,466,446 to Baldwin et al., U.S. Pat. No. 4,373,535 to Hartell, U.S. Pat. No. 4,340,067 to Rettenborg and U.S. Pat. No. 4,327,745 to Ford, Jr. However, experience has shown that blood still leaks through the membrane causing potential contamination to the technician drawing the blood.

In certain instances, the patient's blood pressure is insufficient to pump the blood into the specimen chamber. For these type of patients it is necessary to have a blood gas syringe which can aspirate the blood after the needle is inserted into the artery. The syringes of the prior art which have either an air vent through the piston and/or the membrane typically cannot be used to aspirate the patient's blood. In some instances, such as in U.S. Pat. No. 4,361,155 to Anastasio, the air vent has been connected through a hole in the plunger handle which hole can be covered by the technician's finger and used to aspirate. However, this is inconvenient and not entirely satisfactory because it causes the technician to hold the syringe in an unnatural position, thereby potentially causing the needle to move and damage to the patient's arteries. Other prior art syringes have solved this aspiration problem by allowing a complex mechanism which can be twisted to close the air vent. For example, see U.S. Pat. No. 4,326,540 to Bailey et a. Such devices however require special parts with tight precision requirements in order to be operative, and also result in potential damage to the patient. Other solutions to the problem of being able to aspirate using a blood gas syringe include providing a check valve above the air vent. For example, see U.S. Pat. No. 4,373,535 to Martell. This prior art solution has required special parts, thereby increasing the cost, and did not solve the other problems mentioned above.

Syringes generally are made in large numbers for many medical applications including injecting medicine and aspirating blood. Because of the large numbers of conventional syringes manufactured, the individual components can be inexpensively obtained. It would be of great economic advantage to utilize currently available components in fabricating a syringe which can be used to obtain a blood sample for blood gas analysis.

BRIEF DESCRIPTION OF THE INVENTION

In accordance with one aspect of this invention there is provided a syringe of the type used to obtain a specimen of arterial blood for blood gas analysis comprising a hollow cylinder adapted to having a hollow needle of a type for insertion into an artery affixed to one end thereof and in fluid communication therewith. The syringe further comprises a plunger slideably positioned within the cylinder and an air passage through the plunger sized to allow air to flow in a direction from a specimen chamber formed between the needle end of the cylinder and the plunger through the air passage to the side of the plunger remote from the specimen chamber. Finally, the syringe comprises valve and seat means positioned within said plunger remote from the chamber to prevent air from flowing through the passage into the specimen chamber.

BRIEF DESCRIPTION OF THE DRAWING

One preferred embodiment of the subject invention is hereafter described with specific reference being made to the following figures, in which.

PREFERRED EMBODIMENT OF THE INVENTION

Figure 1:
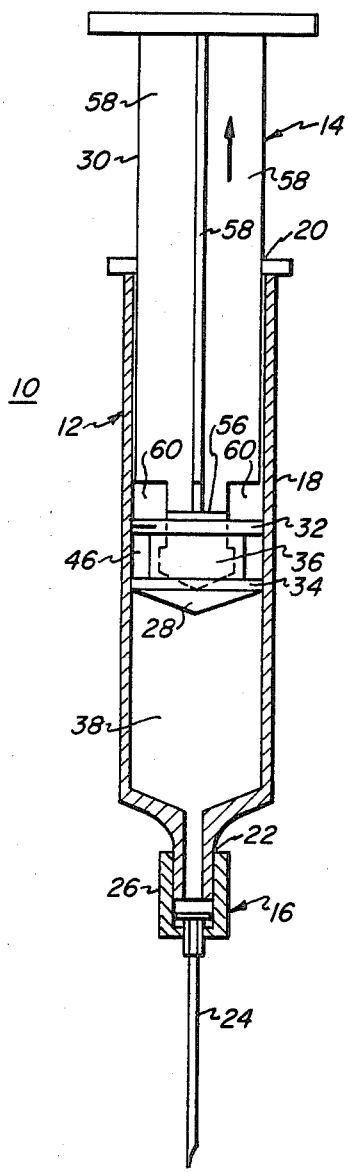
FIG. 1 shows the blood gas syringe of the subject invention.

Referring now to FIG. 1, blood gas syringe 10 is shown and includes a barrel assembly 12, plunger assembly 14 and needle assemly 16. Barrel assembly 12 and needle assembly 16 may be identical to such assemblies commonly available in the marketplace or to assembly shown in for instance U.S. Pat. No. 4,466,446, and manufactured by Marquest Medical Products Inc. of Englewood, Colo. Generally, barrel assembly 12 may be made of a rigid plastic material and includes a cylindrical portion 18 having an open top 20 and a bottom formed into a neck 22 to which the needle assembly 16 is affixed.

Needle assembly 16 includes a hollow needle 24 molded into a compression fitting 26. Fitting 26 is adapted to be fit over neck 22 so that a fluid path exists through needle 24 into the interior of cylindrical portion 18.

Plunger assembly 14 includes a piston 28 and handle 30 affixed to piston 28 in a conventional manner. Handle 30 may be a conventional handle used in syringes, except that the bottom portion thereof interfacing with piston 28 has been narrowed in a manner to be described hereafter.

Piston 28 also may be a conventional state of the art piston used in syringes with certain modifications made thereto to be described hereafter. Generally, piston 28 has an upper rib 32 and a lower rib 34, each sized to be substantially the same size or slightly larger than the inner dimension of cylindrical portion 18. Connecting upper and lower ribs 32 and 34 is a smaller outer diameter body 36 of piston 28. body 36 may be generally hollow, which together with a hole 42 through upper rib 32 remote from the edges thereof, provides a receptacle for affixing handle 30 to piston 28 in a conventional manner.

Assembled in this manner handle 30 may be moved up or down causing a corresponding movement of piston 28. As piston 28 moves up, it causes fluid (air or blood) to enter into needle 24 into a fluid chamber 38. The fluid chamber is that volume defined by the bottom of piston 28, the side walls of cylinder 18 below piston 28 and the portion connecting cylinder 18 to neck 22. On the other hand, when handle 30 is pushed downward causing a downward movement of piston 28, the fluid within chamber 38 is expelled through needle 24.

Figure 2:
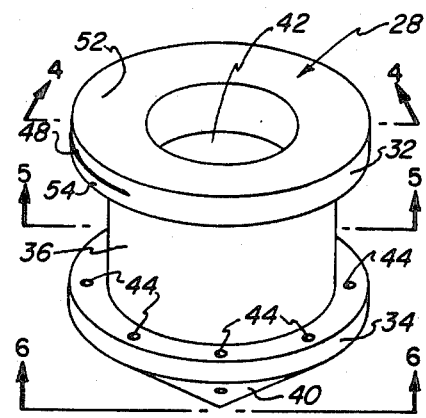
FIG. 2 shows the plunger used in the syringe shown in FIG. 1.

Referring now to FIGS. 2 through 6, the detailed construction of the improvement made to piston 28 will now be described. In FIG. 2, a modified conventional syringe piston 28 is shown. As previously mentioned, piston 28 includes upper rib 32 and lower rib 34 coupled together in an integral structure by body 36. Body 36 is of a smaller diameter than upper rib 32 or lower rib 34 which have the same or slightly larger diameter than the inner diameter of cylindrical portion 18. Thus, an air space 46 (shown in FIG. 1) is formed between body 36 and the walls of cylinder 18. The portion of piston 28 beneath lower rib 34 is shaped as a cone 40 designed to interface with the shape of the top of neck 22 of cylinder 18 shown in FIG. 1. An opening 42 through upper rib 32 is provided into the generally hollow center of body 36 for affixation of handle 30 in a known manner.

Piston 28 is modified over the conventional piston by the provision of a plurality, for instance eight, of air passages 44 extending from cone 40 through lower rib 34. Each of the air passages 44 are positioned so that the air will flow into the air space 46. The diameter of each of the air passages 44 through lower rib 34 should be selected to allow air to readily pass therethrough, but to prevent the passage of blood therethrough. It has been found that a air passage of approximately 0.008 inches in diameter, that is, approximately 0.00005 square inches. is acceptable for this purpose. It is believed that the blood in passing through air passages 44 tends to clot, thereby closing the air passage. This clotting action occurs despite the fact that an anticoagulant, such as Heparin, may be inserted into fluid chamber 38. Eight passages 44 are provided equally spaced around the circumference of lower rib 34 for the purpose of allowing a sufficient area of air passage and for the further purpose of allowing all of the air to be displaced when needle 24 is inserted at an angle into the artery, despite the rotational position of syringe 10.

Figure 4:
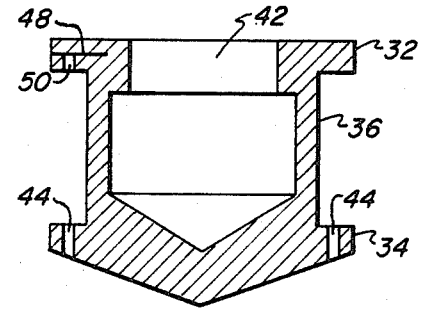
FIG. 4 shows a cross sectional view of the plunger taken across lines 4—4 in FIG. 2.
Figure 3:
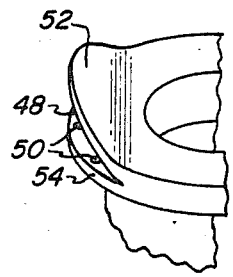
FIG. 3 shows the flap portion of the plunger shown in FIG. 2 in the open position.
Figure 5:
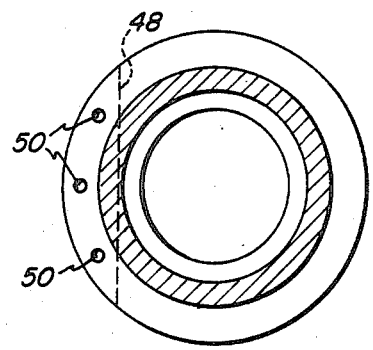
FIG. 5 shows a cross sectional view taken across lines 5—5 of FIG. 2.
Figure 6:
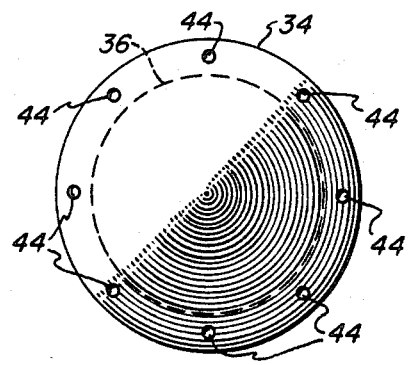
FIG. 6 shows a bottom view taken across lines 6—6 of FIG. 2.

Another modification to plunger 28 is that upper rib 32 is provided with a slit 48, generally between the center and top thereof, extending therein towards opening 42. A plurality of, for instance three, air passages 50 are provided from the bottom of upper lip 32 upwards to slit 48 as best seen in FIGS. 3, 4 and 5. Each of the air passages 50 may also be 0.008 inches in diameter. Because the material of piston 28 is a soft flexible material, such as rubber, slit 48 forms a flap 52 above slit 48 which moves up from the lower portion 54 beneath slit 48. Flap 52 thus acts as a valve closing over a seat formed by portion 54. When flap 52 is raised, as shown in FIG. 3, air can pass through openings 50 from air space 46. On the other hand, when flap 52 is against seat 54, as shown in FIG. 2, air is prevented from passing downward through passages 50 into air space 46.

Referring again to FIG. 1, the bottom portion of handle 30 is shaped so as not to interfere with the opening or closing of flap 52. More specifically, the bottom flange 56 and support brackets 58 adjacent to flange 56 have been cut away so that the diameter of flange 56 and associated brackets 58 are only slightly larger than opening 42. At the same time they are made smaller than the depth of slit 48 creating flap 52. This creates an open area 60 between handle 30 and piston 28. Thus, as flap 52 moves up into open area 60 it does not interfere with handle 30.

In operation, syringe 10 may be used as follows. When the patient has sufficient blood pressure so that chamber 38 can be filled without aspiration, handle 30 is retracted until a desired volume exists within chamber 38. In a conventional syringe, markings exist along the side of cylinder 18 indicating the volume within specimen chamber 38. When handle 30 is first retracted, air enters through needle 24 to fill the void left in chamber 38. Thereafter, needle 24 is inserted into the patient's artery and blood enters into chamber 38 through needle 24 and neck 22. As the blood enters chamber 28, it displaces air which previously existed in chamber 38. This air flows out through passages 44 in lower rib 34 and into air space 46. From there, it flows through passages 50, lifting flap 52 to allow the air to escape. Once the entire volume of chamber 38 has been filled, the blood enters into passages 44 causing them to become closed by the clotting action of the blood and an insufficient amount of blood pressure to force blood through the small diameter passages 44 due to surface tension and friction. Normally, a Heparin tablet, or other anticoagulant material, is placed in chamber 38 to prevent the blood from clotting while in chamber 38. However, because of the small size of openings 50, the blood still clots as it passes therethrough, thereby preventing a significant amount of blood from entering air space 46.

If the patient's blood pressure is sufficient to only partially fill fluid chamber 38 with blood, the technician removes needle 24 from the artery and places it in a conventional stopper. Thereafter, handle 30 may be depressed forcing any remaining air within chamber 38 out through air passages 44 and 50. When cone 40 completely touches the blood in chamber 38, it will no longer be possible to depress handle 30 further, since the blood cannot flow through passages 44.

In either event, by allowing the air to be displaced out of chamber 38 by either the blood pressure filling chamber 38 or partially filling chamber 38 and handle 30 being depressed to evacuate the air, the contamination to the blood gas by the air is minimized. By proper techniques the contamination can be determined and calibration of the testing instruments can occur to eliminate any effect thereof.

In the final mode of operation, where the patient's blood pressure is insufficient to adequately fill chamber 38, handle 30 is fully depressed so that cone 40 rests against the top of neck 22. Needle 24 is then inserted into the patient's artery and handle 30 is withdrawn slowly. In this instance, both the air attempting to pass from above piston 28 into chamber 38 and the wiping action of flap 52 against the inner wall of cylinder 18 forces flap 52 against seat 54. This closes the air passages 50, so that air cannot flow from above piston 28 to air space 46.

As handle 30 is removed from cylinder 18, blood is withdrawn from the artery through needle 24 into chamber 38. Once a sufficient portion of blood has been withdrawn, needle 24 is removed from the artery and placed in a stopper and handle 30 is depressed to remove whatever air exists in chamber 38. Such air may be due to the volume of air in the needle hub and shaft.

What is claimed is:

1. A syringe of a type used to obtain a specimen of blood for blood gas analysis comprising:
    a hollow cylinder providing a specimen chamber adapted to having a hollow needle, of the type for insertion into an artery, affixed to one end thereof in fluid communication therewith, said cylinder having an inner surface;
    a plunger slideably positioned within said inner surface of said cylinder, said plunger including a handle and a piston, and at least one radial rib around said piston in movable contact with said inner surface, said piston having an inner end adjacent said needle, an external end connected to said handle, and an unbroken peripheral piston surface;
    a plurality of air passage and fluid restricter means through said plunger sized to allow air to flow and to restrict the flow of blood in a direction from said specimen chamber and to restrict the flow of blood through said air passage and fluid restricter means to said external end of said piston remote from said specimen chamber and out past said handle, said air passage and fluid restricter means formed between said inner end and said external end of said piston; and
    valve and seat means in fluid communication with said air passage and fluid restricter means and positioned on said piston remote from said specimen chamber to prevent air from flowing through said air passage and fluid restricter means into said specimen chamber;
    said air passage and fluid restricter means for allowing air to flow out of said chamber leaving blood by blocking blood flow out through said air passage and fluid restricter means each said air passage and fluid restricter means having a generally straight channel constructed and sized of substantially small cross section of a length to prevent blood, a liquid from flowing therethrough and allow air, a gas to flow therethrough.

2. The invention according to claim 1, wherein said plunger is of a type having upper and lower seal means sized to slideably engage the inside surface of said hollow cylinder, said air passage including a series of substantially small holes positioned around the periphery and through said lower seal means.

3. A syringe as set forth in 1, wherein each said air passage and blood restricter means is a channel having a generally longitudinal path through said rib and sized having a cross sectional area of generally 0.00005 square inches to prevent blood from flowing therethrough.

4. An arterial syringe having a hollow cylinder means and a plunger of a type used to obtain a blood specimen from an artery for the purpose of performing a blood gas analysis on said specimen comprising; said syringe further being of the type in which the specimen is obtained by arterial pressure forcing blood into the syringe or by aspiration of blood into the syringe by physical movement of said plunger partially out of said hollow cylinder means, said syringe including a hollow cylinder means and having an attachment means adapted for attachment to a hollow needle for affixing said needle to the bottom of said cylinder, said needle and attachment means providing a fluid passage through said needle into said hollow cylinder means; and
    said plunger including a piston with an uninterrupted surface and a handle connected to an upper end of said piston, said plunger slideably positioned within said hollow cylinder means for forming a specimen chamber between said attachment means and said piston, said piston including an upper sealing member connected around said upper end of said piston and lower sealing member connected around a lower end of said piston and said piston connecting the upper and lower said sealing members to form an air space therebetween,
    a plurality of generally channel shaped opening means having substantially small cross sectional area around and through a periphery of the lower said sealing member sized to allow air but not blood to flow therethrough, said opening means for blocking blood flow;
    at least one opening through the upper said sealing member; and
    directional means for allowing air to flow from said air space through said at least one opening and preventing air from flowing through said at least one opening into said air space when said plunger is physically moved partially out of said hollow cylinder means.

5. The invention according to claim 4 wherein said directional means is a valve and seat member, said at least one opening extending from said air space to said seat member.

6. The invention according to claim 5 wherein said valve is formed into one portion of said upper sealing member, said valve is a cut into the side of said upper sealing member.

7. The invention according to claim 13 wherein said piston is fabricated of a soft elastic material.

8. The invention according to claim 7, wherein said flap covers said air passage means when closed, thereby preventing air from flowing from the side of said plunger remote from said speciment chamber to the side of said plunger adjacent to said specimen chamber, and said flap is opened when air flows through said air passage means from said specimen chamber to said external end.

9. The invention according to claim 8 wherein said upper and lower seal means being shaped to form a seal with said inner surface of said cylinder, said lower seal being adjacent to said specimen chamber, said upper and lower seals being coupled by a coupling member smaller in area than the cross sectional area of said upper and lower seal means, whereby an air space is formed between said upper and lower seal means and said coupling member and inner surface of said cylinder, said air passage means including a plurality of openings in said upper and lower seal means between the specimen chamber side and the formed air space and said valve and seat means, said valve and valve seat means formed in said upper seal means.

10. The invention according to claim 9, wherein eight said passage means are used.

11. A syringe of a type used to obtain a specimen of blood for blood gas analysis comprising:
   a hollow cylinder adapted to having a hollow needle, of the type for insertion into an artery, affixed to one end thereof in fluid communication therewith, said cylinder having an inner surface;
   a plunger slideably positioned within said cylinder having an inner end adjacent said needle, an external end, and a peripheral surface;
   a plurality of air passage means through said plunger sized to allow air to flow in a direction from a specimen chamber through said air passage means to said external end of said plunger remote from said specimen chamber, said air passage means formed between said inner end and said external end adjacent said peripheral surface; and
   valve and seat means in fluid communication with said air passage means and positioned within said plunger remote from said chamber to prevent air from flowing through said air passage means into said specimen chamber;
   said air passage means for blocking blood flow, said air passage means is constructed and sized of substantially small cross section having a channel means for preventing blood from flowing therethrough and for aiding in clotting of the blood;
   said plunger is of a type having upper and lower seal means sized to slideably engage the inside surface of said hollow cylinder, said air passage means including a series of substantially small holes positioned around the periphery and through said lower seal means;
   said plunger is an elastic material forming a seal against said inner surface of said cylinder, said valve and seat means being a flap on the end of said plunger remote from said specimen chamber on said upper seal means, said air passage means extending through said plunger to said flap.

12. An arterial syringe of a type used to obtain a blood specimen from an artery for the purpose of performing a blood gas analysis on said specimen, said syringe further being of the type in which the specimen is obtained by arterial pressure forcing blood into the syringe or by aspiration of blood into the syringe, said syringe including a hollow cylinder means and having an attachment means adapted for attachment to a hollow needle for affixing said needle to the bottom of said cylinder, said needle and attachment means providing a fluid passage through said needle into said cylinder means; and
   a plunger slideably positioned within said cylinder means for forming a specimen chamber between said attachment means and said plunger, said plunger including an upper sealing member and lower sealing member and means connecting said upper and lower sealing member to form an air space therebetween, the improvement comprising:
   a plurality of opening means having substantially small cross sectional area around the periphery of said lower sealing member sized to allow air but not blood to flow therethrough, said opening means for blocking blood flow;
   at least one opening through said upper sealing member;
   directional means for allowing air to flow from said air space through said at least one opening and preventing air from flowing through said at least one opening into said air space;
   means is a valve and seat member, said at least one opening extending from said air space to said seat member;
   said valve is formed into one portion of said upper sealing member; and
   said valve is a cut into the side of said upper sealing member.

13. The invention according to claim 12 wherein at least one said opening through said upper sealing means includes a plurality of holes between said air space and said seat member.

* * * * *